Dec. 30, 1941. H. A. VERSCHUREN Plant Pat. 497
ROSE PLANT
Filed July 7, 1941
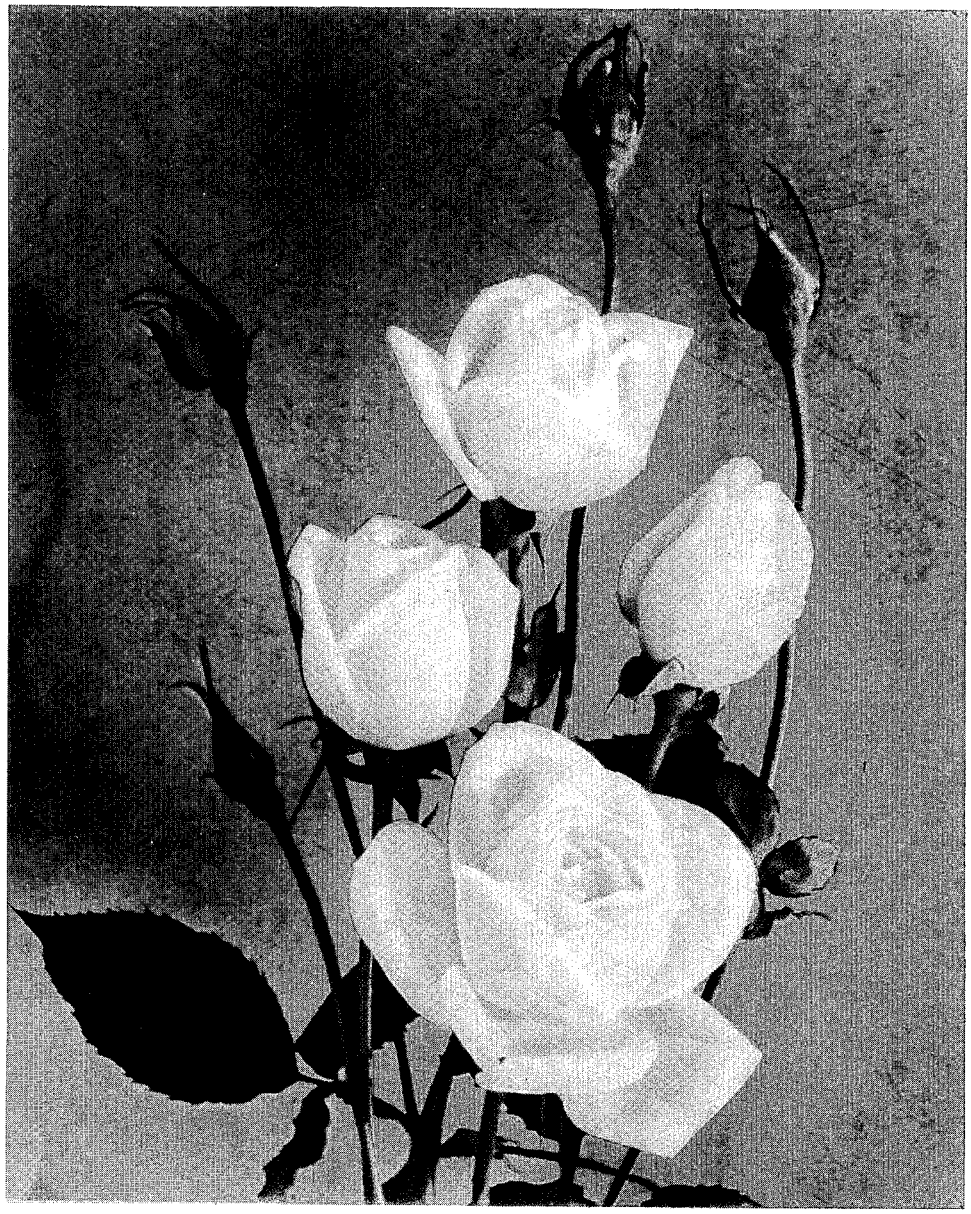
INVENTOR
Hendrikus A. Verschuren
By Orville M. Kile
Plant Pat Agt.

Patented Dec. 30, 1941

Plant Pat. 497

UNITED STATES PATENT OFFICE

497

ROSE PLANT

Hendrikus Antonie Verschuren, near Uden, Netherlands, assignor to Henry A. Dreer, Incorporated, Philadelphia, Pa., a corporation of New Jersey Application July 7, 1941, Serial No. 401,369

1 Claim. (Cl. 47—61)

The present invention relates to a new and distinct variety of rose plant of the hybrid tea class, having resulted as a definite cross between two well known varieties in an effort to produce a superior yellow rose. The pollen parent was Max Krause and was crossed upon the seed parent Julien Potin. This cross pollination work was carried on by me on my premises in Haps, Holland.

The new variety has been asexually reproduced for several years and its distinguishing qualities appear to be firmly fixed. Tests have been made both in Europe and in the United States of America.

The most outstanding feature of this new variety is the intense and pleasing perfume of its blossoms. Its perfume is very much like that of the old Marechal Niel rose which has for many years been a favorite in mild climates.

This new variety is a very vigorous grower and is practically disease proof. It is hardy without special protection in the climate of middle Europe where it was originated. This quality enables it to be grown in more rigorous climates than can be done with the Marechal Niel.

A common failing among yellow rose varieties has been their lack of good form of the opened blossom. This failing has been largely overcome in the present variety, since the blossoms are almost globular, holding their form with little flattening when mature.

Although the blossom is not unusually large, it is composed of an unusually large petalage for yellow roses, and therefore makes a very compact rose. This feature no doubt contributes greatly to the almost perfect form of the blossoms.

The original illustrations accompanying this application show in full color four tight buds and four opening buds and flowers of this new variety, together with their stems and foliage.

In the following description, plate references indicate Ridgway's Color Standards and Nomenclature. Where no references are given, the usual dictionary term is intended.

*The plant*

Growth: Particularly vigorous. Hardy in temperate climates such as that of England.

Form: Bush.

Disease resistance: Very resistant to diseases, no disease having yet been found on the plants of this variety.

Stems: Strong; stiff; upright. Color, Yellowish Oil Green (Plate V), usually overlaid with bronze or red ranging from Snuff Brown (Plate XXIX) to Deep Corinthian Red (Plate XXVII).

Thorns: Many; long; sharp; irregularly spaced; approximately Acajou Red (Plate XIII); have large base; extend at right angles to stem or slightly downward. No spines or prickles appear on the main stems.

Foliage:

*Leaves.*—Compound, with 3 to 5 leaflets.

*Quantity.*—Moderate.

*Size.*—Medium. Terminal leaflet averages 2½ inches in length by 1⅜ inches in width.

*Texture.*—Heavy; leathery.

*Color.*—Upper surface approximately Dark Cress Green (Plate XXXI); under surface grayish green. Edge frequently red, approximately the same color as the thorns.

*Shape.*—Oval with acuminate apex. Margin finely and sharply serrate. Wavy and inclined to fold at midrib.

*Aspect.*—Glossy on upper surface; dull on lower surface.

*Rachis.*—Above grooved and reddish tinged; below green, smooth except for an occasional small prickle.

*Stipules.*—Long; narrow; clinging.

*The flower*

Blooming habit: Continuous throughout the season.

Flowers borne: Usually borne singly and on long stems.

Quantity of bloom: Very abundant.

Fragrance: Exceedingly fragrant with a pleasing odor somewhat similar to that of the Marechal Niel rose.

Lasting quality: Good.

Bud:

*Peduncle.*—Medium length and size; smooth; straight; erect.

*Sepals.*—Usually simple, sometimes slightly branched.

*Size.*—1½ to 2 inches in length.

*Form.*—Very long; pointed.

*Opening.*—Even.

*Color.*—Almost uniformly Strontian Yellow (Plate XVI) with slightly darker shading at base of petals.

Bloom:

*Size.*—Medium to large. Usually 3½ to 4 inches in diameter, but occasionally produces some very large flowers.

*Form.*—Globular form which is retained for several days, after which it opens into deep cup shape. The outer petals roll backward slightly.

*Petalage.*—Full. In September 40 to 45 petals. In the spring the petalage often is 60, the average for the entire season being 45 to 50.

*Color.*—The newly opened flower is a clear, uniform yellow which lies between Lemon Chrome (Plate IV) and Strontian Yellow (Plate XVI). However the shadows of the deep center make it appear considerably darker. As the flower ages, the edges of the petals become much lighter, approximately Barium Yellow (Plate XVI), while the base remains a shade approximately as at first. This produces a rose which is pale yellow on the edges with a deep yellow center.

Petals:

*Texture.*—Substantial.

*Appearance.*—Silky.

*Shape.*—Almost round.

*Arrangement.*—Imbricated.

*Persistence.*—Drop off cleanly.

Reproductive organs:

*Pistils.*—Many; bunched; hairy. *Styles,* Martius Yellow (Plate IV) merging into red. *Stigmas,* approximately Rose Red (Plate XII), tipped with Baryta Yellow (Plate IV).

*Stamens.*—Many; surround bunched pistils; uneven lengths. *Filaments,* Cadmium Orange (Plate III) at the base, merging into Strontian Yellow at the top. *Anthers,* approximately Deep Chrome (Plate III).

Having thus disclosed my invention, I claim:

The new and distinct variety of hybrid tea rose plant herein shown and described, characterized particularly by its vigorous growth and productivity; its hardiness in temperate climates; its great disease resistance; its attractive, long-pointed bud; and its blossom of clear yellow color, compact globular form, large petalage, and intense fragrance of the Marechal Niel type.

HENDRIKUS ANTONIE VERSCHUREN.